(12) United States Patent
Fritsch et al.

(10) Patent No.: US 8,805,547 B2
(45) Date of Patent: Aug. 12, 2014

(54) EXTRA-COCHLEAR IMPLANTED HEARING AID DEVICE

(75) Inventors: Michael H. Fritsch, Lincoln, NE (US); John H. Fritsch, Lincoln, NE (US)

(73) Assignee: Domestic Legacy Limited Partnership, Indianapolis, IN (US)

( * ) Notice: Subject to any disclaimer, the term of this patent is extended or adjusted under 35 U.S.C. 154(b) by 1940 days.

(21) Appl. No.: 11/451,715

(22) Filed: Jun. 13, 2006

(65) Prior Publication Data

US 2007/0005117 A1     Jan. 4, 2007

Related U.S. Application Data

(60) Provisional application No. 60/695,309, filed on Jun. 30, 2005.

(51) Int. Cl.
*A61N 1/05* (2006.01)

(52) U.S. Cl.
USPC ............................ 607/137; 607/57

(58) Field of Classification Search
USPC ............................ 607/55–57, 137
See application file for complete search history.

(56) References Cited

U.S. PATENT DOCUMENTS

| | | |
|---|---|---|
| RE31,031 E | 9/1982 | Kissiah, Jr. |
| 4,532,930 A | 8/1985 | Crosby et al. |
| 4,617,913 A | 10/1986 | Eddington |
| 4,819,647 A | 4/1989 | Byers et al. |
| 4,832,051 A | 5/1989 | Jarvik et al. |
| 4,892,108 A | 1/1990 | Miller et al. |
| 5,123,422 A | 6/1992 | Charvin |
| 5,653,742 A | 8/1997 | Parker et al. |
| 5,674,264 A | 10/1997 | Carter et al. |
| 5,755,747 A | 5/1998 | Daly et al. |
| 6,112,124 A | 8/2000 | Loeb |
| 6,151,526 A | 11/2000 | Tzviskos |
| 6,205,360 B1 | 3/2001 | Carter et al. |
| 6,301,505 B1 | 10/2001 | Money |
| 6,374,143 B1 | 4/2002 | Berrang et al. |
| 6,408,855 B1 | 6/2002 | Berrang et al. |

(Continued)

FOREIGN PATENT DOCUMENTS

| | | |
|---|---|---|
| EP | 1574181 A1 | 9/2005 |
| WO | WO 2004/054474 A1 | 7/2004 |

OTHER PUBLICATIONS

Badi et al. "Development of a Novel Eighth-Nerve Intraneural Auditory Neuroprosthesis." The Laryngascope, 113, May 2003, pp. 833-842.*

(Continued)

*Primary Examiner* — Eric D. Bertram
(74) *Attorney, Agent, or Firm* — E. Victor Indiano; Indiano Law Group, LLC

(57) ABSTRACT

An extra-cochlear hearing aid implant is characterized by a pad having a plurality of electrode prongs that extend therefrom and which are adapted to provide an electrical stimulus to hearing cells within the cochlea. The electrode pad is adapted to be placed onto endosteum overlying the cochlea in an "extended soft surgery" technique. The prongs are configured to pierce the endosteum and extend into the cochlea. In one form, the extra-cochlear hearing aid implant also includes hollow tubules that extend from the pad and which are adapted to supply and withdraw neurotrophic proteins and other materials in a fluid into and from the cochlea, and also to provide electrical stimulus to the hearing cells.

27 Claims, 10 Drawing Sheets

(56) References Cited

U.S. PATENT DOCUMENTS

| | | |
|---|---|---|
| 6,428,484 B1 | 8/2002 | Battner et al. |
| 6,496,734 B1 | 12/2002 | Money |
| 6,537,800 B1 | 3/2003 | Karube et al. |
| 6,549,814 B1 | 4/2003 | Strutz et al. |
| 6,556,870 B2 | 4/2003 | Zierhofer et al. |
| 6,575,894 B2 | 6/2003 | Leysieffer et al. |
| 6,636,768 B1 | 10/2003 | Harrison |
| 6,648,914 B2 | 11/2003 | Berrang et al. |
| 6,724,902 B1 | 4/2004 | Shennib et al. |
| 6,946,851 B2 | 9/2005 | Lee et al. |
| 7,044,942 B2 | 5/2006 | Jolly et al. |
| 7,063,708 B2 | 6/2006 | Gibson et al. |
| 7,146,227 B2 | 12/2006 | Dadd et al. |
| 2001/0031974 A1 | 10/2001 | Hadlock et al. |
| 2002/0029074 A1 | 3/2002 | Treaba et al. |
| 2003/0045921 A1 | 3/2003 | Dadd et al. |
| 2003/0097121 A1 | 5/2003 | Jolly et al. |
| 2004/0115241 A1 | 6/2004 | Calhoun et al. |
| 2004/0172118 A1 | 9/2004 | Gibson |
| 2004/0182707 A1* | 9/2004 | Jardemark et al. ............ 204/451 |
| 2005/0015133 A1 | 1/2005 | Ibrahim et al. |
| 2005/0080473 A1 | 4/2005 | Gibson et al. |
| 2006/0264897 A1 | 11/2006 | Lobl et al. |
| 2007/0060815 A1 | 3/2007 | Martin et al. |

OTHER PUBLICATIONS

Badi, Arunkumar N., *Development of a Novel Eighth-Nerve Intraneural Auditory Neuroprosthesis*; Laryngoscope 113: May 2003.

Cochlear Collaborative Research Report, "Research Toward an Endosteal Electrode Array", (Pau & Rodriguez) 2004.

Acta Otolaryngol (Stockh) 1988; 449: 55-57, Cochlear implant. Treatment of deaf people with cochlear implant—Reults of an 8-channel extracochlear implant.

Laryngoscope 113: May 2003; Development of a Novel Eighth-Nerve Intraneural Auditory Neuroprosthesis.

Acta Otolaryngol (Stockh) 1989; 107: 210-218; Development of Cochlear-wall Implants for Electrical Stimulation of the Auditory Nerve.

*The Journal of Laryngology and Otology*; Jun. 1985; vol. 99, pp. 549-553; Extracochlear eight-channel electrode system.

*Otolaryngologic Clinics of North America*; vol. 19, No. 2, May 1986; Extracochlear Sixteen-Channel Electrode System.

*The Laryngoscope*; 107: Aug. 1997; Implantation of the Lateral Cochlear Wall for Auditory Nerve Stimulation.

*The American Journal of Otology*; vol. 8, No. 3, May 1987: Titanium Implants in the Otic Capsule: Development of a New Multichannel Extracochlear Implant.

Part Two—The Human Ear; Fig. 72 (Date Unknown, Definitely Prior Art).

Allen M. Cassell, "Ultrasensitive Carbon Nano-Electrode Biosensor Technology", Center for Nanotechnology, University of California at Santa Cruz, Moffit Field, California, Apr. 22, 2004.

"Hearing with a Cochlear Implant",www.bionicear.com, Feb. 24, 2005.

"Hear Now and Always", www.Cochlear Americas.com.

"Med-EL Products Overview", www.medel.com. Feb. 24, 2005.

* cited by examiner

EXTRA-COCHLEAR IMPLANTED HEARING AID DEVICE

I. RELATED APPLICATIONS

This U.S. non-provisional patent application claims the benefit of and/or priority to U.S. provisional patent application Ser. No. 60/695,309 filed Jun. 30, 2005 entitled "Extra-Cochlear Implanted Hearing Aid Device", the entire contents of which is specifically incorporated herein by reference.

II. FIELD OF THE INVENTION

The present invention relates to hearing aid devices and, more particularly, to an implantable extra-cochlear hearing aid device.

III. Background of Invention

Hearing loss can occur for many reasons and/or from many causes but such hearing loss can generally be classified as two types, namely conductive and sensorineural. This invention revolves around treatment of sensorineural hearing loss.

For conductive hearing loss, the middle ear bones or eardrum fail to transmit sound energy into the inner ear. Either surgery to correct the conductive loss or conventional hearing aids worn in the ear or auditory canal amplify incoming sound enough to overcome the conductive loss so that the sound energy reaches the cochlea and its hair cells.

A hearing aid functions as an amplifier by magnifying received acoustic signals. Once magnified, the acoustic signal travels along the auditory pathway normally. If potential augmentable hearing is present, a conventional hearing aid is the initial device of choice. The greatest limitation of a hearing aid is not technologic; rather, it relates to the number of surviving functional cochlear hair cells. If only a small percentage of the cochlear hair cells are viable, their stimulation by amplification of the sound signal cannot completely compensate for the hearing loss caused by the nonfunctional hair cells.

Sensorineural hearing loss occurs due to the absence or the destruction of the hair cells in the cochlea which are needed to transduce the sound energy into auditory nerve electrical impulses. Those persons who are afflicted with mild, moderate or severe sensorieneural hearing loss may benefit from hearing aids. Others, with more profound losses are unable to derive benefit from conventional hearing aids and thus a cochlear implant may be used.

A cochlear implant differs from a hearing aid in that the auditory signal-sound wave received by the device is processed (not just amplified) and converted into an electrical impulse. Cochlear implants are intended for patients with severe to profound sensorineural hearing loss. Sound and speech are captured by a microphone worn behind the ear and sent to a speech processor. The processor may be incorporated with the microphone and worn externally behind the ear or worn remotely, such as at the belt level. The speech processor digitally encodes the speech with use of various encoding strategies, depending on the manufacturer and model of the implant. The speech processor then sends the encoded signal to a transmitter. The transmitter is located behind the ear and overlies the implanted stimulator. The transmitter is held in place by a magnet attached to the implanted stimulator. The transmitter then sends the signal transcutaneously to the implanted stimulator, which in turn directly stimulates the spiral ganglion cells and axons of the cochlea by means of an electrode array.

In view of this, cochlear implants bypass the hair cells in the cochlea by presenting electrical stimuli directly to the dendrites, the ganglia or ganglion cells of the auditory nerve located adjacent the modiolar wall of the cochlea. When triggered, the ganglia send nerve impulses to the brain via the auditory nerve leading to the perception of sound. Cochlear implants are known as "intra-cochlear" implants when they are inserted into the cochlea. If they are external to the cochlea and stimulate the ganglia from externally, then the implants are known as "extra-cochlear" implants.

Particularly, intra-cochlear implants are placed within the cochlea and usually into the scala tympani of the cochlea. Such an intra-cochlear implant may be placed within the scala vestibuli of the cochlea. The preferred placement, however, is in the scala tympani.

However, there are various problems with intra-cochlear hearing aid implants. One of the problems concerns the cochlear implantation process itself. There is a great chance of intra-cochlear damage by penetration of the intra-cochlear implant electrode through multiple membranes of the cochlea, with consequent destruction of the small organ of Corti and the other anatomic structures within the cochlea, as well as giving rise to degeneration of neurites and spiral ganglion cells. Since the ganglion cells carry the electronic stimulus to the cochlear nerve and the brain, then if the ganglion cells are not present, a poor result would be expected from the cochlear implant. Thus, maximal preservation of the internal anatomy of the cochlea and its related structures is paramount.

However, because an intra-cochlear implant is generally large and stiff, as it is coiled through the cochlea, it may damage the cochlear contents. Acting as a bulldozer, it may penetrate through, rip and even strip away the membranes, including everything from the osseous spiral lamina, the vestibular ligament, the spiral ligament, the basalar membrane, the vascular stria, and, the Corti organelle of hearing and the endosteum. Such would then definitely impact the cochlear nerve and the spiral ganglion that are in the modiolus. The spiral ganglion is an important structure because this is where residual nerve cells in sensory hearing loss reside and are those nerve cells that relay transmission of the implant's electrical impulse to the cochlear nerve and eventually to the brain. Thus, it should be appreciated that the intra-cochlear implantation technique can be very traumatic and reduce the ability of the implant to successfully stimulate residual neural elements in patients with hearing loss.

In view of the above, current intra-cochlear implants are slimmer, more flexible and designed to help overcome the stiffness problems of the initial generations of cochlear implants, which caused great degrees of trauma. The degree of trauma may be less, but it is still considerable.

Another problem with intra-cochlear implants concerns the number of electrodes on the implant. The cochlea is organized "tonotopically". In other words, specific tone frequencies are found at specific points along the length of the cochlea. High frequencies are found at the cochlea basal turn which contains the largest cochlear duct membranes and their adjacent ganglion and nerve cells. Low frequencies are located at the very apex, the smallest cochlear turn. Thus, when one inserts a cochlear implant close to the round window in the usual cochleostomy fashion, it first will go past the parts that stimulate high frequencies, then advance through the mid-frequencies and then to the lower frequencies.

Because of the tonotopic anatomy, if one puts an electrical stimulus impulse into the cochlea that is broadly disbursed, it is going to impact spiral ganglia that cover a wide tonotopic range, and will not be as tonally specific. Rather than sampling a very narrow frequency spectrum of the tonotopic arrangement it would then stimulate a very wide swath of frequencies. The more electrodes present, the more stimulation electrode spots there will be on the implant resulting in more frequency differentiation and sound understanding. Also, the closer that the stimulating electrodes are placed to the residual ganglion cells, the more likely that the electrodes are to be focused on the ganglion of interest for that specific tone. Conversely, the further away the electrodes are placed, the more likely that the stimuli will get dispersed and not impact the ganglia of interest but rather, impact ganglion over a wide tonal section.

Extra-cochlear implants were first seen in the late 1970s-80s as another manner of providing a hearing aid implant and, in general, were popularized prior to intra-cochlear implants. An extra-cochlear implanted hearing aid device is implanted outside the cochlea and the bulk thereof stays outside of the cochlea in contrast to intra-cochlear implants that are placed into and coil inside the cochlea. Hence, the surgical approach and electrode design of prior art extra-cochlear implants do not enter directly into the coils of the cochlea by the round window cochleostomy approach, as is the case for intra-cochlear implants.

The extra-cochlear electrodes at that time were basically placed on the unaltered or minimally altered bone of the cochlea and then secured to the bone. Electrical signals had to be transmitted through the bone and then through the scala vestibuli and/or scala tympani to reach the neurites and spiral ganglia nerve cells.

Various problems existed with these early extra-cochlear implants. First, it took an extraordinary amount of electrical stimulation energy to stimulate the spiral ganglia nerve cells appropriately. Second, there was dispersion of the electrical energy, which caused the electrical signals to impact a large area of the cochlea which contains a large number of ganglia, as opposed to a small specific point on the cochlea. Moreover, extra-cochlear implants were positioned too far from the targeted ganglia, causing difficulties in receiving the frequency differentiation. Known prior art implants covered only a very limited part of the cochlea because they were only surgically placeable on the lateral side of the cochlea. Anatomical considerations only permitted the surgeon to gain access to the lateral side. Surgeons did not, and presently do not, have access to easily place implants on the interior side of the cochlea because this region is the inside of the skull.

One type of prior art extra-cochlear implant is described in U.S. Pat. No. 6,549,814 issued to Strutz et el. ("Strutz"). Strutz uses a flattened blade-like electrode that is slid into a tissue pocket. Strutz creates an opening in the cochlear bone down to the endosteum and then forms a pocket by surgical tissue de-lamination of the endosteum from the bony cochlear wall. The Strutz electrode appears to be generally flat on the bottom with some studs. The flat configuration is useful as it allows the electrode to fit into the narrow pocket.

However, Strutz's device and implantation technique has several major impractical standpoints. Strutz describes a six to twelve millimeter (6-12 mm) tunnel to create the pocket in which the implant is placed. While six to twelve millimeters appears to be short, this length may provide a difficult and long distance to physically dissect blindly inside of a coiled snail-shell structure. The endosteum is quite fragile and prone to tearing when stretched. Since one is not looking directly at the endosteum as one makes the tunnel with an instrument tip, it would be quite difficult to avoid tearing the endosteum.

Twelve millimeters would be an extreme stretch, because one would have to go around the curve of the cochlea while dissecting the microscopic sized pocket. Strutz even states that it could go so deep that it could be 180 degrees around the inside of the cochlea. However, it would be nearly impossible to create a 180 degree pocket since one would most likely rupture through the endosteum and enter into the cochlea during the process of creating the pocket. Also, the other delicate internal cochlear structures could be damaged in the process.

Another prior art extra-cochlear implant is disclosed in Gibson et al., U.S. Published Patent Application No. 2005/0080473 ("Gibson"). The Gibson electrode is similar to Strutz's in that it appears to have somewhat of a flat surface. Moreover, Gibson also discusses inserting the extra-cochlear implant into a pocket.

Gibson's device and implantation technique would have exactly the same difficulties as Strutz. In Gibson's preferred embodiment, the extra-cochlear implant has a maximum length of seven to ten millimeters (7-10 mm); a width of 0.6 mm; and a thickness no greater than 0.2 mm. The Gibson extra-cochlear implant also has a "stop member" that serves to both arrest progression of the implant inwards and helps to advance the electrode as a "handle". Again, the Gibson device suffers from the same difficulties in dissection of 7 to 10 mm of depth pocket beyond the cochleostomy in a soft surgery technique that would most probably lacerate the cochlea's osseous spiral lamina.

Another extra-cochlear electrode design is described in an article by Professors H. W. Pau and M. M. Rodriquez. The Pau and Rodriquez article shows a flat electrode design that is placed in an "extra-luminar cavity between the spiral ligament and the lateral bony wall of the cochlea". In essence, it comprises a flat, non-penetrating electrode that is insertable into a pocket, similar to the Strutz and Gibson designs. This electrode design is believed to originate from Cochlear Corp. and Profs. H. W. Pau and M. M. Rodriguez et al., as the article is published in the 2004 Research Report by Cochlear Corp., Melbourne, Australia. The Pau and Rodriquez device suffers from the same drawbacks as the Strutz and Gibson designs.

In summary, the major difficulties with the pocket techniques discussed in Strutz, Gibson and the Pau/Rodriguez/Cochlear Corp. references are that one is limited firstly in length of what one can do because of the snail shell-like curve of the cochlea and secondly, with the curvature of the cochlea as one is dissecting the pocket, one will most probably dissect through the endosteum and then push the electrode intra-cochlearly, all the while, destroying residual anatomy.

It is thus evident from the above that there is a need for an improved extra-cochlear hearing aid implant.

It is also evident from the above that there is a need for an improved manner of implanting an extra-cochlear hearing aid implant.

IV. SUMMARY OF THE INVENTION

The present invention comprises an extra-cochlear hearing aid implant. The extra-cochlear hearing aid implant includes an electrode pad that is adapted to be placed onto the cochlear endosteum in a minimally invasive manner. The electrode pad includes an array of electrically conductive, penetrating prongs, each one of which extends outwardly from the electrode pad. The prongs are meant to penetrate through the endosteum into one of the cochlear scalae. The prongs are designed to conduct an electrical stimulus to the end of the prong so that the electrical stimulus can electrically stimulate a nearby dendrites, ganglion and/or small ganglia group.

In one form, the present extra-cochlear implant also includes hollow tubules for introducing and removing fluid into the interior of the cochlea. The tubules are tiny hollow tubes that are conceptually similar to hypodermic needles. The tubules are likewise penetrating in nature.

The present extra-cochlear implant gathers electrical energy through a trans-cutaneous induction coil disposed between the electrode array and a receiver stimulator in an external speech processor.

The prongs and/or tubules of the present invention may be varied in length and/or curved to facilitate optimal positioning within the cochlea. This will help bring the stimulating electrode prongs closer to the ganglion cells. The closer that the stimulating electrodes are placed to the residual ganglion cells, the more likely they are to be focused on the ganglion of interest for that specific tone. The further away they are, the more likely that the stimuli will get dispersed and not impact the ganglia of interest but rather, impact ganglion over a wide tonal section. Therefore placing the tubules and prongs close enough to the ganglion will result in improved differentiation and sound understanding.

The present extra-cochlear hearing aid implant is thus adapted to be placed onto the outside of the cochlea utilizing an "on-lay" procedure wherein the "pad" of the electrode is placed exteriorly of the cochlea, and the prongs and tubules are inserted laterally through the endosteum. This allows the prongs and tubules to be positioned close to the spiral ganglion, but not touching to prevent damage to the sensitive anatomy. "Soft surgery" describes a gentle technique, discussed in the prior art, of removing bone down to the endosteum prior to inserting an intra-cochlear implant and creating an opening of only 1-2 millimeters (mm) in diamter. The 1-2 mm opening is known as a "cochleostomy". The extra-cochlear implant pad is much larger. Thus, a much larger area of "soft surgery" is needed, and will be referred to as the novel "extended soft surgery" technique. This "extended soft surgery technique" includes drilling an area of bone overlying an area of the cochlea onto which the pad of the extra-cochlear implant is to be implanted. This exposes not just a small 1-2 mm sized cochleostomy area of endosteum, but a long strip of underlying endosteum large enough to receive the electrode pad.

Since the prongs and tubules are arranged side by side in a hairbrush or comb-like orientation, this orientation along with the extended soft surgery technique, allows one to place the bulky pad exterior to the cochlea while having a large number of prongs and tubules inside the cochlea. This is because the aggregate diameter or width of the prongs and tubules are being expressed along the outside length of the cochlea, rather than bundled together and squeezed inside the cochlea.

The fluid tubules (conduits) allow fluid to be transported into the electrode pad and then distributed to the various infusion tubules. A small pump with a reservoir for refilling is used to supply the device. A trans-cutaneous tube can provide direct access to the reservoir or pump. Small catheter tubing can sequentially lead from the fluid source to the electrode backbone, pad and tubules. The supply source and tubing, in one form, has a self-sealing, detachable valve attachment to the electrode and/or implant device.

The fluid can be a multiple of different chemicals and cells. For example, the fluid can contain such things as neurotrophins, antioxidants, chemicals, vasoactive compounds, growth factors, anti-glycemics, insulin, medications, nucleotides, amino-acids, nutrients, cells, stem cells and "nanobots" or nano-robots. This infused fluid is used to help promote nerve cell growth and improve transmitted sounds within the ear. For example, the infusion of the substances would cause nerve cell growth such that one or more prongs become wrapped in nerve tissue and very easily and efficiently transmit its impulse with minuscule amounts of electricity directly to the nerve.

V. BRIEF DESCRIPTION OF DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

VI. DETAILED DESCRIPTION

Figure 1:
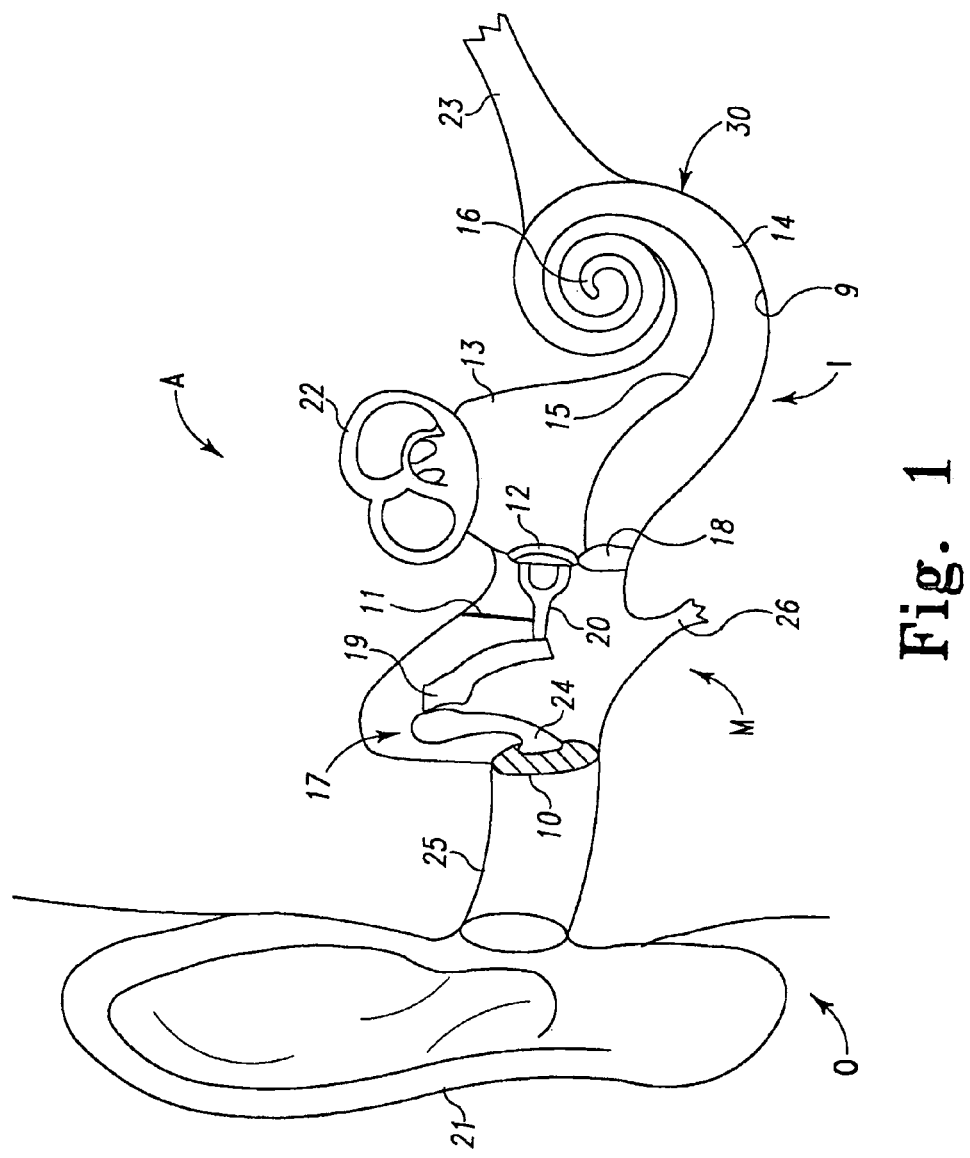
FIG. 1 is a sectional view of the anatomy of the human auditory system.

Referring to FIG. 1, there is shown a sectional view of the anatomy of the human auditory system A. At a macro level, the human auditory system A consists of the outer ear 0, the middle ear M and the inner ear I.

The outer ear 0 includes the pinna or auricle 21 and the ear canal 25 that provides communication from the outer ear 0 to the middle ear M. The middle ear M includes the eardrum (tympanic membrane) 10, the ossicles 17 consisting of the hammer (malleus bone) 24, the anvil (incus bone) 19, and the stirrup (stapes bone) 20, with the stapes tendon 11 providing support for the ossicles 17, and the Eustachian tube 26.

The middle ear M also includes the oval window 12 to which is attached the stirrup 20 for communication therethrough and the round window 18 which provides communication with the scala tympani 14.

The inner ear has two main components which are the semi-circular canals 22 and the cochlea 30. The endosteum 9 lines the entire inner surface of the inner ear I. The cochlea 30 includes the scala tympani 14, the scala media 15 and the scala vestibuli 13. The perilymphatic chamber of the vestibular system has a wide connection to scala vestibuli 13, which in turn connects to scala tympani 14 by an opening called the helicotrema 16 at the apex of the cochlea 30. Scala tympani 14 is then connected to the cerebrospinal fluid of the subarachnoid space by the cochlear aqueduct. The cochlear nerve 23 extends from the cochlea 30 to the brain.

The present extra-cochlear hearing aid implant (or extra-cochlear implant) is configured and/or adapted to have a pad positioned on the external surface of the endosteum, external to the interior of the cochlea 30. Portions of the implant, such as prongs or tubules extend into the interior of the cochlea in order to conduct/provide electrical stimulation to auditory receptor cells. The present extra-cochlear implant has the greatest portion of its size positioned onto the cochlea but has finer elements extending into the cochlea where electrical stimulation and fluid carrying tubules are desired.

Figure 2:
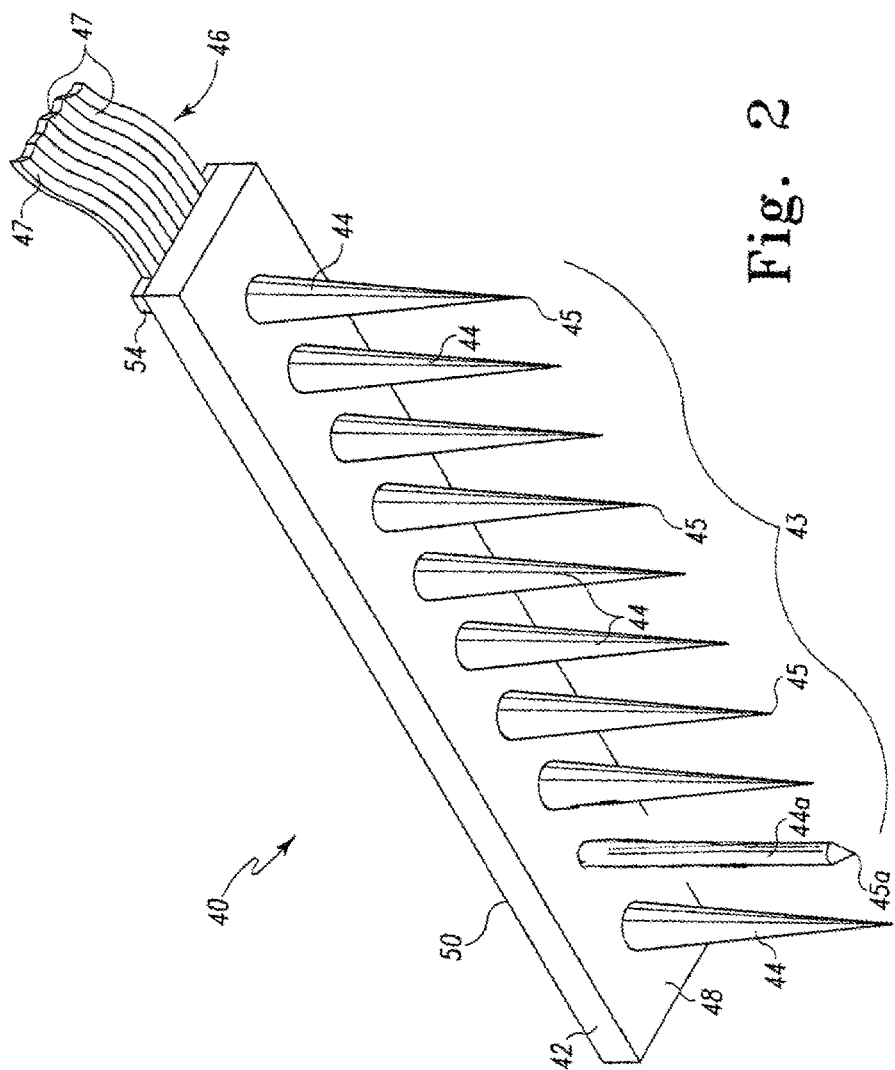
FIG. 2 is perspective view of an exemplary embodiment of an extra-cochlear hearing aid implant in accordance with the principles of the present invention.
Figure 3:
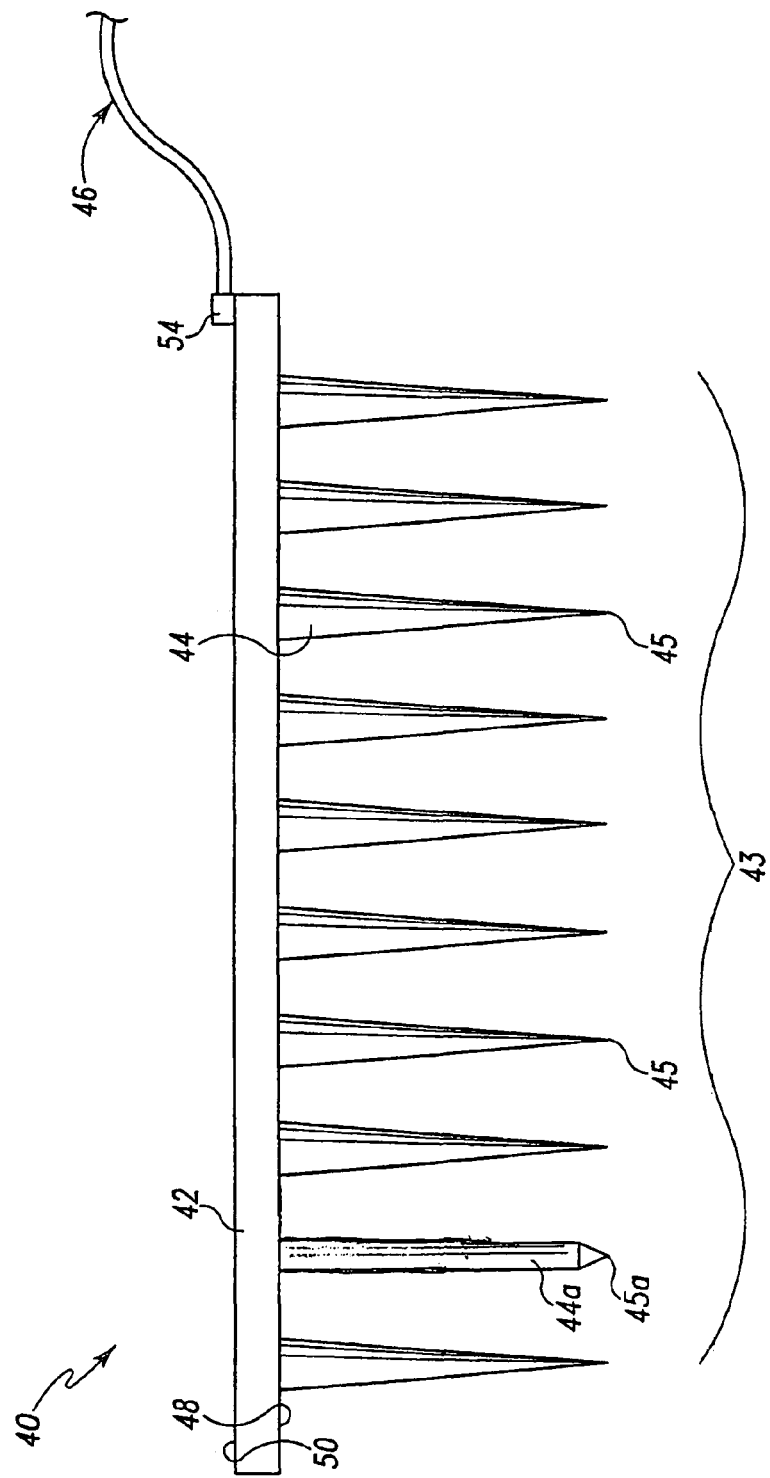
FIG. 3 is a side view of the extra-cochlear implant of FIG. 2.

Referring now to FIGS. 2 and 3, there is shown an embodiment of an exemplary extra-cochlear hearing aid implant, generally designated 40, fashioned in accordance with the principles of the present invention. The extra-cochlear implant 40 includes a pad/on-lay/carrier, or the like 42 fashioned from a biocompatible material. Examples of such biocompatible materials include platinum, titanium and conductive nano materials. Preferably, but not necessarily, the pad 42 is sufficiently flexible so as to permit the pad 42 to lie onto, and conform to the contours of the cochlea and, particularly, the endosteum overlying the cochlea.

The pad 42 includes a lower surface 48 and an upper surface 50. An electrode array or plurality 43 of electrode prongs 44 extend from the lower surface 48 of the pad 42 in a direction generally perpendicular to the plane of the lower surface 48 of the pad. The prongs 44 are conductive members whose purpose is to conduct an electrical stimulus to the distal end 45 of the prong 44. The prongs 44 of the electrode array 43 are situated on the pad 42 in a comb-like manner. Each prong 44 may have a generally tapering shape that terminates in a pointed distal end 45. In this manner, the electrode prongs 44 are piercing members, i.e. they are adapted to pierce the lining endosteum of the cochlea and extend into the cochlea so that an electrical stimulus provided to the prongs 44 can electrically stimulate a nearby ganglion or small ganglia group of a portion of the cochlea. In determining the "shape" of the prongs, a balance should be achieved between strength and size. For purposes of illustration, prong 44a is shown as a nail-shaped prong 44a having a generally cylindrical shaft portion and a tapered, conical distal end 45a. In this regard, a nail-shaped prong having a generally cylindrical shape with a tapered end, would have the asset of requiring little space on the pad due to the small size of its base, when compared to a conical shaped prong. As such, a large number of nail-shaped prongs could be placed on an electrode pad of a given size.

However, a very thin, cylindrical prong would be relatively weaker than a broad based conical prong, in terms of piercing strength and ability to resist bending or deformation upon being driven through the endosteum. As such, a "tapering" shape, that would likely comprise a conical prong having a relatively large height to base diameter ratio is believed to achieve the best balance between strength and space savings.

It should be appreciated that the prongs 44 may take different shapes than conical such as cylindrical or tubular. The particular shapes of the prongs 44 are dictated primarily by their twin functions of serving as "nails" to pierce through the endosteum, and as electrodes to carry current to a location remote from the pad 42. The prongs 44 may all be the same shape or may be different shapes. As well, the length of the prongs may be long or short. Long prongs are used to get as close to the neural element as possible. Shorter lengths may be used to limit trauma.

Preferably, the distal ends 45 of the prongs 44 are close to the ganglion cells, but not touching the ganglion cells. However, some prongs 44 may end within the fluids of the cochlea, touch the osseous spiral lamina, touch the modiolus structures, penetrate the endosteum or bone on the modiolus side, contact the spiral ganglia or even contact the cochlear nerve. Additionally, the number of prongs 44 may vary from that shown. The number of prongs 44 may depend on various factors. Prongs penetrating the modiolar bone would be sufficiently strong to prevent bending or breaking.

In all cases, the electrode prongs 44 are penetrating in type and are needle-like (and preferably shaped like conical needles) so that they do not take up much space. They can be placed close together so that they give very precise stimulation points to the spiral ganglion and cochlear nerve. The lengths of the electrode prongs may be varied and can vary among the array of prongs 44 and also from one electrode design to another particular design, depending on the specific needs and the limitations. The prongs 44 may also be curved. Further, the prongs 44 may use nano-materials so that nano-tubes, quantum wires, and quantum cables may be used to carry electrical signals.

Figure 4:
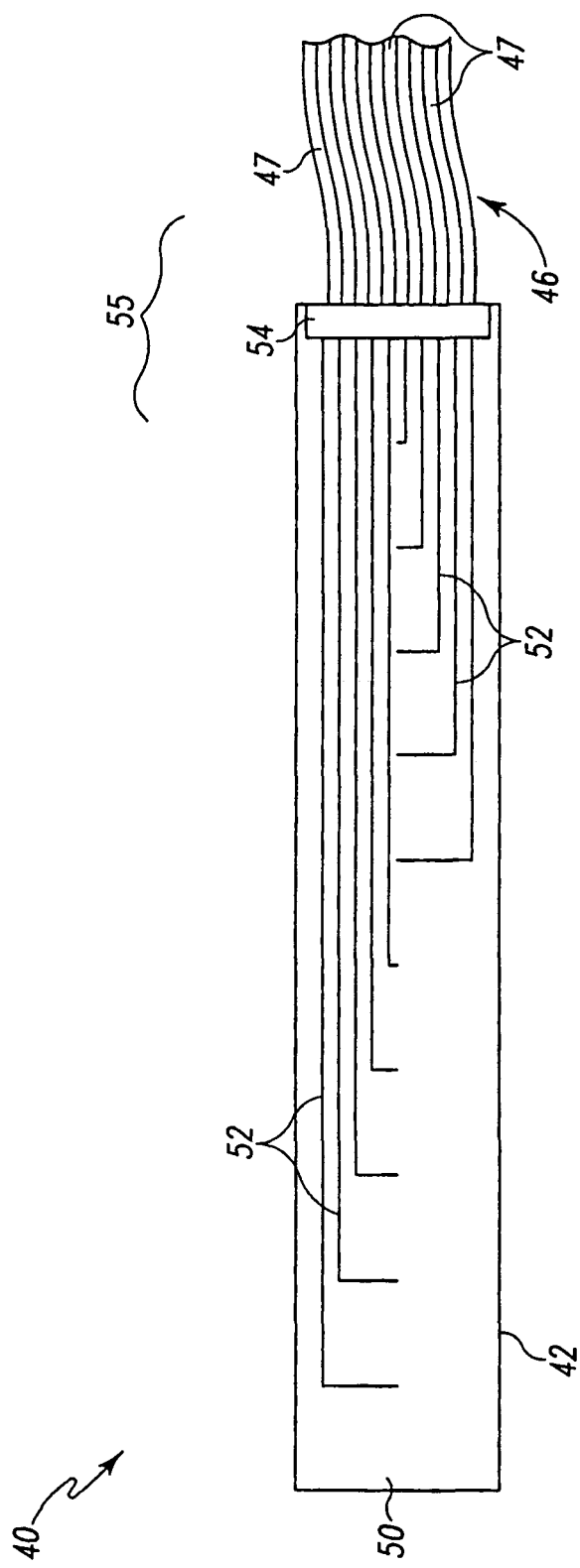
FIG. 4 is a top view of the extra-cochlear implant of FIG. 2.

As best seen in FIG. 4, the pad 42 carries a plurality of electrical traces or conductors 52 each one of which corresponds with and connects to an individual prong 44. A connector 54 provides electrical communication to/with a ribbon cable or the like 46 composed of individual wires or electrical conductors 47. Thus, an electrical stimulus is provided to individual prongs 44 through the individual wires 47 and the electrical traces 52. The connector area 54 along with the cable 46 and various fluid supply tubules (FIG. 6, #122, 116; FIG. 7, #117, 122) make up the "backbone" area 55.

Of course, other manners of individually providing an electrical stimulus to each prong 44 are contemplated. For instance, a single conductor may provide a multiplexed signal to the electrical traces 52 in order to provide an electrical stimulus to the individual prongs as appropriate and/or necessary.

Figure 5:
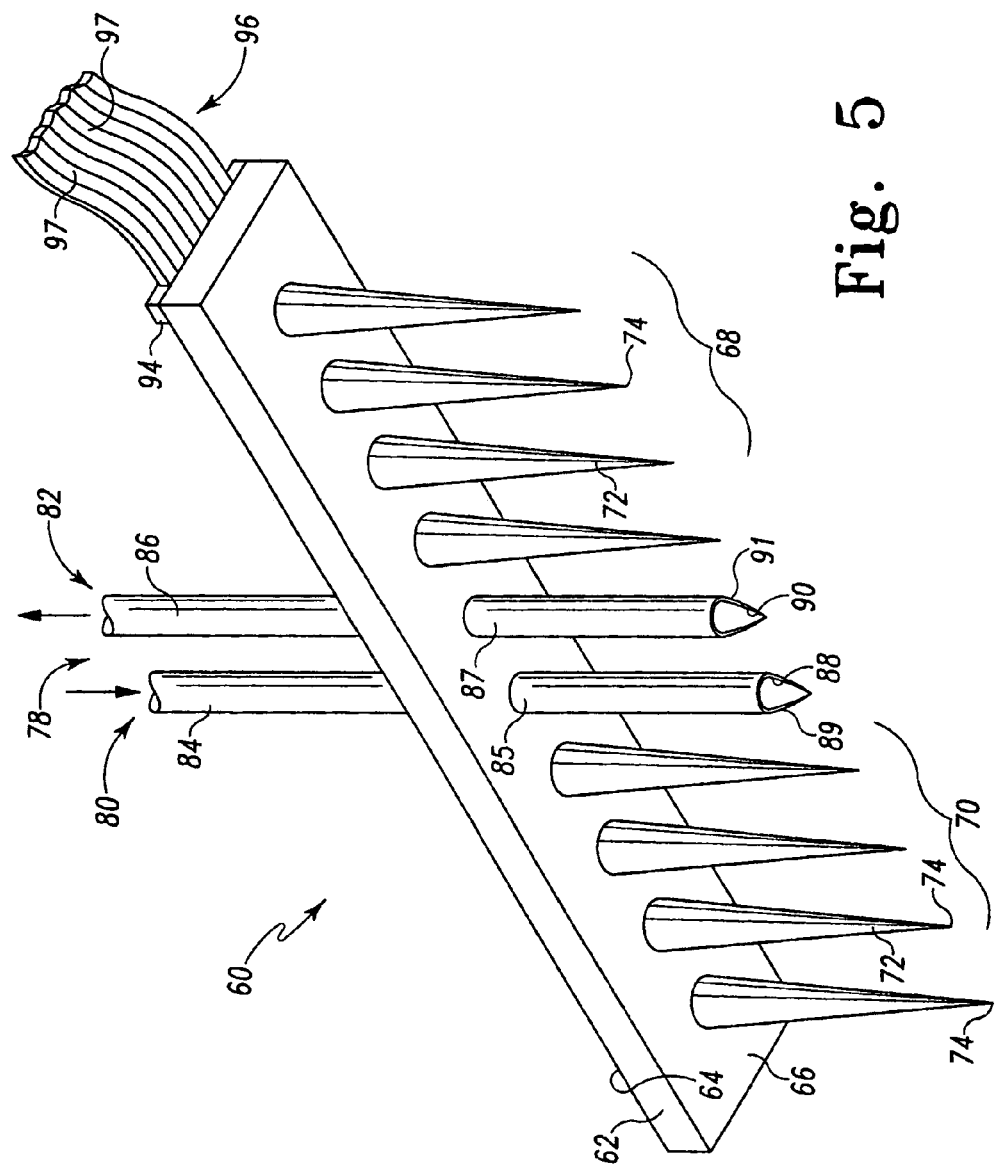
FIG. 5 is a perspective view of another exemplary embodiment of an extra-cochlear hearing aid implant in accordance with the principles of the present invention.

FIG. 5 shows another embodiment of an exemplary extra-cochlear hearing aid implant, generally designated 60, fashioned in accordance with the principles of the present invention. The extra-cochlear implant 60 includes a pad/on-lay/carrier or the like 62, fashioned from a biocompatible material. Preferably, the pad 62 is sufficiently flexible or shaped to permit the pad 62 to lie onto the contours of the cochlea and, particularly, the endosteum overlying the cochlea.

The pad 62 defines a lower surface 66 and an upper surface 64. An electrode array is defined by a first plurality 68 of electrode prongs 72 and a second plurality 70 of electrode prongs 72. The prongs 72 extend from the lower surface 66 of the pad 62. The prongs 72 are conductive members that are provided for conducting an electrical stimulus to the end of the prong 74. The prongs 72 of the electrode arrays 68, 70 are situated on the pad 62 in a comb-like manner and may be considered as one electrode array. Each prong 72 has a generally tapering or cylindrical shape that terminates in a pointed end 74. In this manner, the electrode prongs 72 are piercing members, i.e. they are adapted to pierce the outer portion of the cochlea and extend therein so that an electrical stimulus provided to the prongs 72 can electrically stimulate a nearby ganglion or small ganglia group of a portion of the cochlea.

Again, it should be appreciated that the prongs 72 may take different shapes than conical such as tubular. The prongs 72 may all be the same shape or may be different shapes. As well, the length of the prongs may be long or short. Long prongs are used to get as close to the neural element as possible. Shorter lengths may be used to limit trauma. As such, the length(s) of the prongs 72 should be chosen to be long enough to extend far enough into the interior of the cochlea so as to have the distal ends 74 of the prongs disposed as closely as possible to the ganglion cells, but short enough so as not to pentrate through or otherwise cause trauma to the opposite wall of the cochlea, and the ganglion and other tissue disposed at or near the opposite wall.

Preferably, the distal ends 74 of the prongs 72 are close to the ganglion cells, but not touching. However, some may end within the fluids of the cochlea, touch the osseous spiral lamina, touch the modiolus structures, penetrate the endosteum or bone on the modiolus side, contact the spiral ganglia or even contact the cochlear nerve. Additionally, the number of prongs 72 may vary from that shown. The number of prongs 72 may depend on various factors, many of which are dictated by size limitations imposed by the cochlea, and size constraints imposed by the construction of the prongs 72.

In all cases, the electrode prongs 72 are penetrating in type and are needle-like so that they do not take up much space. They can be placed close together so that they give very precise stimulation points to the spiral ganglion and cochlear nerve. The lengths of the electrode prongs may be varied and different from one another and also from one electrode design to another particular design, depending on the specific needs and the limitations. The prongs 72 may also be curved. Further, nano-materials may be used to carry electrical signals.

As a further feature, the penetrating prongs and tubules are coated with an insulating material layer so that only the area will conduct electrical impulses to the target area. The insulating coating extends from the pad area, where the prongs and tubules originate, along the length and up to the tip. At the tip, the underlaying conductive material of the prong or tubule is exposed so that an electrical signal stimulus passing from the extra-cochlear pad to the intra-cochlear prong does not dissipate into the intra-cochlear fluids before reaching the prong tip positioned near the neural tissue target. The insulation may be made of a conventional material or a nano-material. In a further embodiment, the tubules may act as both fluid conduits and electrical conduits. In that case, the tubules would be insulated up to, or near, the tip area. It is planned that neural growth to the tubules would directly connect the tubules to the neural tissue near the tip, where neurotrophins and other stimulating materials or cells enter the cochlea. The insulating layer protects against dissipation of the electrical stimulus traveling from the pad down the tubule and out into the cochlear fluids before getting to the tip area where the nerve endings have grown onto the tubule tip.

While not seen in FIG. 5, the pad 62 carries a plurality of electrical traces or conductors in like manner to the FIG. 4 electrical traces 52 of the extra-cochlear implant 40 wherein each one of the electrical traces corresponds with and connects to an individual prong 72. A connector 94 provides electrical communication to/with a ribbon cable or the like 96 composed of individual wires or electrical conductors 97. Thus, an electrical stimulus is provided to individual prongs 72 through the electrical traces of the pad 60.

The extra-cochlear implant 60 also includes a fluid system 78 for delivering fluids to the interior of the cochlea, and, in some cases, removing fluids from the interior of the cochlea. Particularly, the extra-cochlear implant 60 has tubules such as inflow tubule 80 and outflow tubule 82. The inflow tubule 80 includes a first portion 84 extending from the upper portion 64 of the pad 62, and a second portion 85 extending from the lower portion 66 of the pad 62. Outflow tubule 82 includes a first portion 86 extending from the upper portion 64 of the pad 62 and a second portion 87 extending from the lower portion 66 of the pad 62.

The tubules 80, 82 are tiny hollow tubes that are conceptually similar to hypodermic needles and thus are adapted to allow fluid to flow therethrough. As indicated by the arrows, the inflow tubule 80 provides a tube through which a fluid can flow into the interior of the cochlea while the outflow tubule 82 provides a tubule through which a fluid can flow out of the interior of the cochlea. As such, the tubules 80, 82 include hollow passageways 88, 90 through which neurotrophin, or other material containing fluid can be introduced into and excess fluid withdrawn from the interior of the cochlea.

Figure 6:
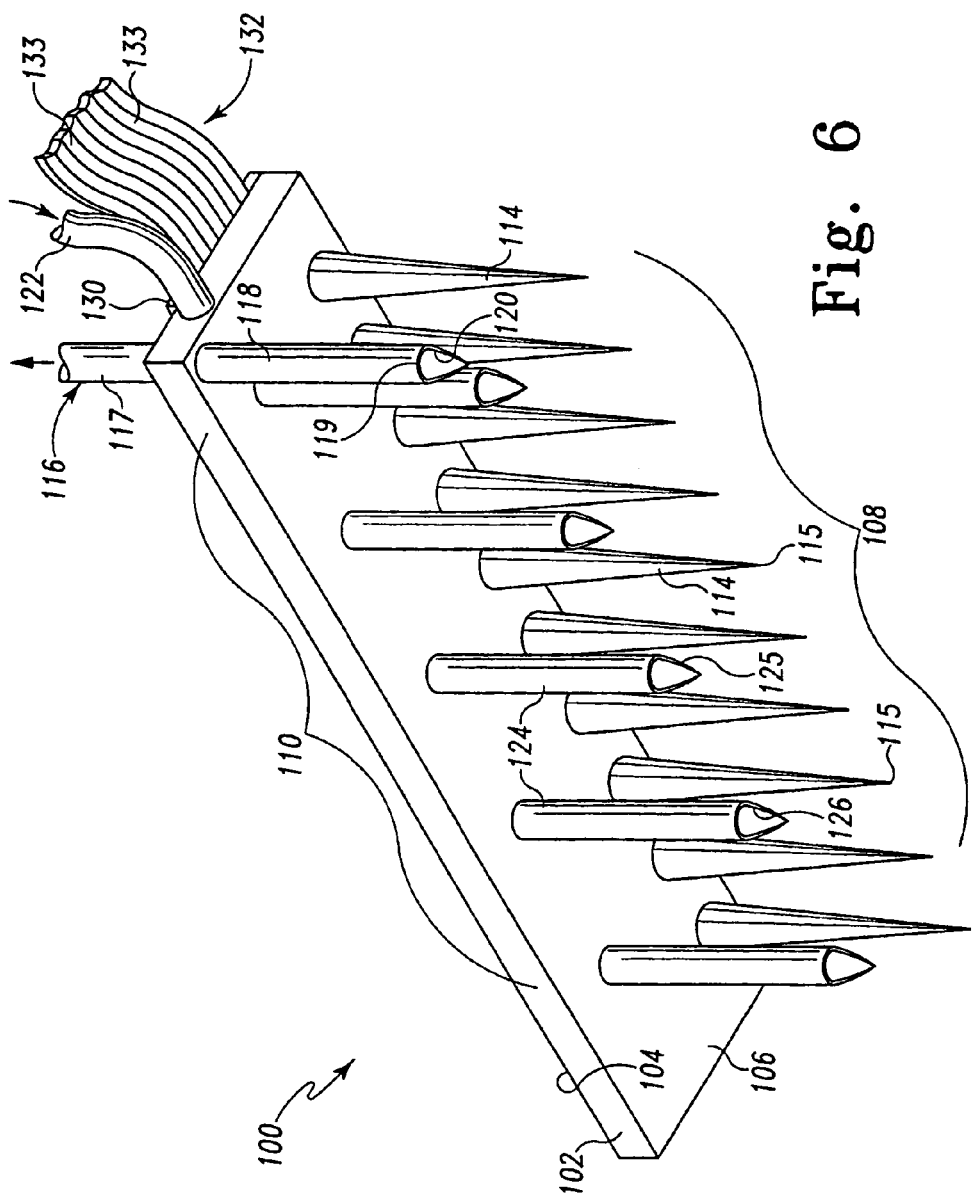
FIG. 6 is a perspective view of another exemplary embodiment of an extra-cochlear hearing aid implant in accordance with the principles of the present invention.
Figure 7:
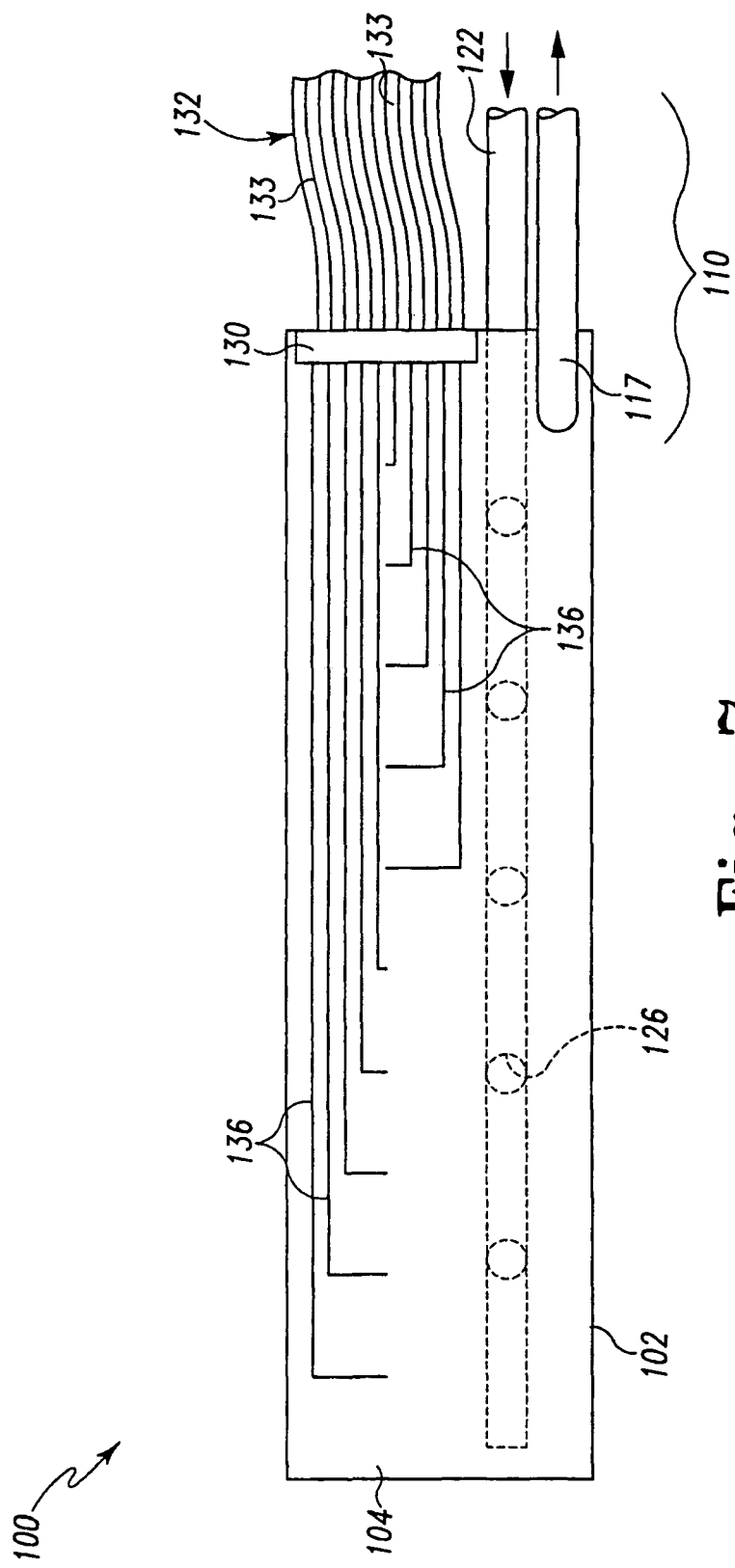
FIG. 7 is a top view of the extra-cochlear implant of FIG. 6.

Referring to FIGS. 6 and 7, there is depicted yet another exemplary embodiment of an extra-cochlear implant generally designated 100, fashioned in accordance with the principles of the present invention. The extra-cochlear implant 100 includes a pad/on-lay/carrier 102, or the like, fashioned from a biocompatible material. Preferably, but not necessarily, the pad 102 is flexible or shaped such that the pad 102 may lie onto and assume the curvature of the contours of the cochlea and, particularly, the endosteum overlying the cochlea.

The pad 102 includes a lower surface 106 and an upper surface 104. An electrode array or plurality 108 of electrode prongs 114 extend from the lower surface 106 of the pad 102. The prongs 114 are conductive members whose purpose is to conduct an electrical stimulus to the end of the prong. The prongs 114 of the electrode array 108 are situated on the pad 106 in a comb-like manner. Each prong 114 has a generally tapering or cylindrical shape that terminates in a pointed end 115. In this manner, the electrode prongs 114 are piercing members, i.e. they are adapted to pierce the outer portion of the cochlea and extend therein so that an electrical stimulus provided to the prongs 114 can electrically stimulate a nearby ganglion or small ganglia group of a portion of the cochlea.

Again, it should be appreciated that the prongs 114 may take shapes different than conical such as cylindrical or tubular. The prongs 114 may all be the same shape or may be different shapes. As well, the length of the prongs may be long or short. Long prongs are used to get as close to the neural element as possible. Shorter lengths may be used to limit trauma. Preferably, the distal ends 115 of the prongs 114 are close to the ganglion cells, but not touching. However, some may end within the fluids of the cochlea, touch the osseous spiral lamina, touch the modiolus structures, penetrate the endosteum or bone on the modiolus side, contact the spiral ganglia or even contact the cochlear nerve. Additionally, the number of prongs 114 may vary from that shown. The number of prongs 114 may depend on various factors.

The penetrating electrode prongs 114 are penetrating in type and are needle-like so that they do not take up much space. They can be placed close together so that they give very precise stimulation points to the spiral ganglion and cochlear nerve. The lengths of the electrode prongs may be varied and different from one another and also from one electrode design to another particular design, depending on the specific needs and the limitations. The prongs 72 may also be curved. Further, nano-materials like quantum wires, quantum cables and nanotubes may be used to carry electrical signals.

As seen in FIG. 7, the pad 104 carries a plurality of electrical traces or conductors 136, in like manner to the FIG. 4 electrical traces 52 of the extra-cochlear implant 40, wherein each one of the electrical traces 136 corresponds with and connects to an individual FIG. 6 prong 114. A connector 130 provides electrical communication to/with a ribbon cable or the like 132 composed of individual wires or electrical conductors 133. Thus, an electrical stimulus is provided to individual prongs 114 through the electrical traces 136 of the pad 104.

The extra-cochlear implant 100 also has a fluid system 110 for supplying and withdrawing neurotrophin containing fluid from the cochlea. Particularly, the extra-cochlear implant 100 has a plurality of fluid supply tubules 126 extending from FIG. 6 underside 106 of the pad 102. The tubules 126 are tiny hollow tubes that are conceptually similar to hypodermic needles and thus are adapted to allow fluid to flow therethrough. As such, each tubule 126 includes a piercing FIG. 6 distal end 119 and a FIG. 7 axially extending hollow passageway or bore 126. Each FIG. 7 tubule 126 is in fluid communication with a fluid inlet tube 122 that extends through the pad 104. The fluid inlet tube 122 allows an inflow of the neurotrophin containing fluid to the plurality 113 of fluid supply tubules 124, as represented by an arrow adjacent the fluid inlet tube 122.

As shown in FIG. 6, the fluid system 110 also has a fluid withdrawal tubule 116 that, as represented by an arrow adjacent the tubule 116, allows an outflow of the neurotrophin or other material containing fluid. The tubule 116 has a first portion that extends from the upper side 104 of the pad 102 and a second portion 118 that extends from the under side 106 of the pad 102. The second portion 118 of the tubule 116 has a tiny hollow tube that is conceptually similar to a hypodermic needle and thus is adapted to allow fluid flow therethrough and, as such, includes a piercing end 119. The tubule 116 also has a hollow passageway or bore 120.

The fluid conduit 122 shown in FIG. 7 will allow fluid to be transported into the electrode pad 104 and then distributed to the various infusion tubules 126. The withdrawing or egress fluid conduit 117 would be connected to the hollow fluid egress tubule 118 (FIG. 6) that pulls fluid out of the cochlea. This would be a benefit of using the extra-cochlear verses the intra-cochlear electrode because in addition to the wires, there is a fluid-containing conduit or possibly several fluid containing conduits that will also take up space. Since the pad and backbone (where the electrical and fluid distribution is going to occur) are extra-cochlear, one is not as space-limited as one would be with an intra-cochlear implant, where all of the fluid and electrical distribution channels must fit within the interior of the cochlea.

From the various exemplary embodiments of an extra-cochlear hearing aid implant constructed according to the present principles, it can be appreciated that the importance of having the implanted electrode prongs and fluid tubules penetrating needle-like and close to the spiral ganglion, but not touching, when implanted is that no internal anatomy is destroyed. By simply placing these prongs and tubules spike-like through the endosteum and into the fluids of the cochlea an atraumatic, tissue preservation method is practiced. The tubules and prongs can be placed away from pertinent anatomy like the Osseous Spiral Lamina, Organ of Corti, and cochlear duct so that the remaining anatomy is undisturbed. For example, the prongs and tubules preferably penetrate only into the scala tympani or scala vestibuli and penetrate through perilymph fluid only, not anatomic structures. The length of the tubules and prongs are designed to reflect the distance from the endosteum to the inner structures and be protective by not destroying sensitive anatomy in a "bulldozer" fashion.

The materials used to make the prongs and tubules can be metals that are micro-cast and/or tooled and also printed. Also, new materials such as carbon "nanotubes" and nanotube-based "quantum wire" and "quantum cables" can be used. The carbon-based nanotechnology is capable of conducting electricity even better than ordinary metals. These wires and cables are like or similar to those manufactured by Richard Smalley at Rice University, and discribed by Allen M. Cassell in "Ultra Sensitive Carbon Nano-Electrode Biosensor Technology," Center for Nanotechnology, University of California at Santa Cruz, Moffit Field, Calif. 22 Apr. 2004.

One benefit of using nanotechnology for the intra-cochlear portion of the present device is that in addition to the nano-wires, there is a fluid-containing conduit or possibly several fluid containing conduits that will also take up space. Since the smaller wires, cables, filaments and tubules of nanotechnology take up less space, the overall diameter of the electrode can be made to have a sufficiently small diameter to still fit into the cochlea. Components of the present device that are disposed inside the cochlea, such as the electrodes and the tubes, are limited by the absolute, finite size of the internal cochlea, so it is important to miniaturize the components as much as possible. Nano-cables and wires help to achieve the miniaturization.

Moreover, since the prongs and tubules are arranged hairbrush or comb-like next to each other, with placement (implantation) using an on-lay extended surgery technique as further described below, one can have a larger number of prongs and tubules. This is because the aggregate diameter or width of the prongs and tubules is being expressed along the outside length of the cochlea, rather than if they were bundled all together and squeezed inside the cochlea.

The closer the prong tips are to the ganglion cells and nerve, the more specific of a target for the electrode simulation pulse of electrical energy. It is more likely to hit its target because it is closer. When one compares the present prongs to the Strutz or the Gibson blades lying external to the endosteum, the electrode stimulation pulses delivered by the Strutz or Gibson devices would be much more diffused and dispersed, since the electrical stimulus has to travel through the diameter of the cochlea. The electrical stimulus delivered by the Strutz and Gibson devices has to penetrate through the fluid compartment of the cochlea, as well as the endosteum. That will require a greater amount of electricity or power to give the electrode enough "juice" to get through to the target. This greater electrical power requirement will deplete the battery much more quickly than is likely to occur with the Applicant's device.

The fluid delivery systems may deliver different types of chemicals and/or cells (such as neurotrophins, neurotropins, antioxidants, chemicals, vasoactive compounds, growth factors, antibiotics, antiglycemics, insulin, medications, nucleotides, amino-acids, nutrients, cells, stem cells, and "nanobots" or nano-robots). Among the purposes for the infusing such substances are to attract and give rise to nerve growth from the spiral ganglion and cochlear nerve towards the actual stimulating prong or adjacent tubule, improve the health of the remaining cells, alter growth of cells and to create new cell and organelle growth.

For example, the infusion of the substances would cause nerve cell growth resulting in one or more prongs becoming wrapped in nerve tissue and very easily and efficiently transmit its (their) impulse with minuscule amounts of electricity directly to the nerve. The purpose of the chemicals, neurotrophins, infused cells, such as stem cells, is to provoke, nurture, feed, stimulate, and seed cellular growth of new internal cochlear anatomy. The new anatomy can be either as replacement of damaged anatomy or, as wholly new structures in new areas not found in normal cochlear anatomy.

In another embodiment, the stimulating prongs or adjacent prongs and tubules have a slow release compound or mechanism related to them. Either by placing a paste, coating, bonding, attaching a bulbous or shaped deposit, impregnating the material used to construct the prongs and tubules itself, or filling a hollow prong or tubule, the compound is connected with the electrode. The slow release compound or mechanism is filled with chemicals or cells (neurotrophins, antioxidants, growth stimulants, stem cells, etc.). Slowly dissolving or mechanically liberating these substances over a period of time accomplishes the neural growth or cell/organelle growth. An example of such a mechanism for slow release is a porous "Buckey Ball" of carbon atoms filled with the desired substance attached to the prongs and tubules and slowly leaking through the openings in the Buckey Ball. In this embodiment, the electrode may or may not have any supply reservoir and tube system connected with it. Rather, the chemicals and/or cells are delivered through the slow release mechanism by itself. The slow release mechanism could also be used in addition to the fluid infusion in the same electrode.

The slow release dissolving mechanism is also useful to keep the prongs and tubules patent and free from obstruction during the insertion process. No cellular debris would plug the inside of the hollow tubules or prongs since the slow release compound would shield against blockage.

The openings in the hollow prongs and tubules may take various forms. A single opening at the tip is one embodiment. An opening or several openings on the sides of the prongs and tubules is another embodiment. The openings may actually form a sieve-like mesh construction of the prongs and tubules. Further, two or more mini-tubules may be bonded together to form the prongs and tubules. The openings may vary from prong and tubule to prong and tubule.

The electrodes and its parts are constructed of metals, noble-metals, plastics, fiberoptics, carbon-based compounds, bonding agents, welds, printed circuits, gels, gases powders, slow and fast timed-release materials, nano-technology, nano-fibers, nanotubes, nanoconductors, quantum wires, nano-materials, and "nano-bots" or nano-robots.

Figure 8:
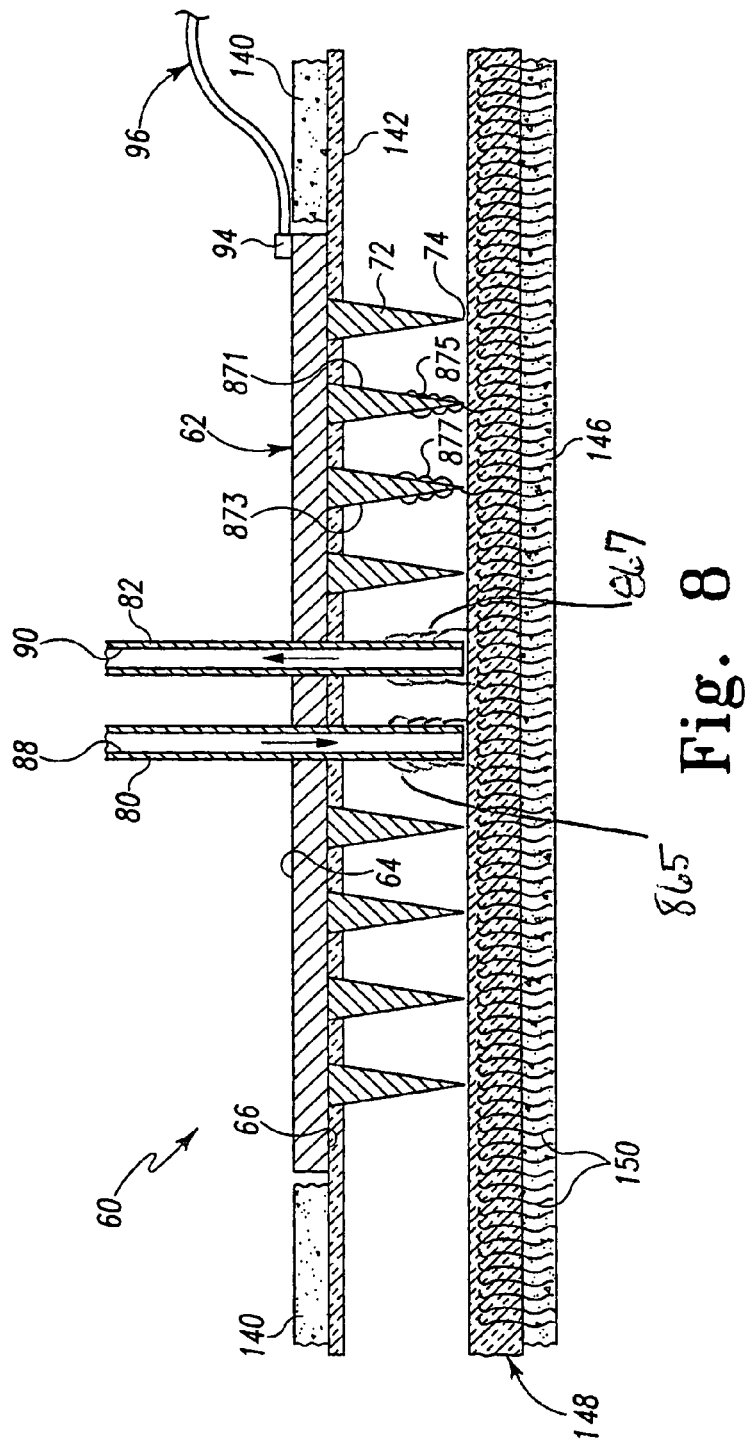
FIG. 8 is a cross-sectional side view of the extra-cochlear implant of FIG. 2 positioned on the endosteum of the cochlea after surgical treatment thereof.

With reference to FIG. 8, a method for implanting or placing the present extra-cochlear implant will be discussed. It should initially be appreciated that the extra-cochlear implant 60 shown in FIG. 8 represents any embodiment of extra-cochlear implant fashioned in accordance with the present principles.

The electrode pad with the prongs and tubules is applied to the cochlea by a surgical technique that would lay the pad, "on-lay", onto the endosteum 142. FIG. 8 schematically shows the "on-lay" concept. This "on-lay" technique and electrode position are distinctly different from the prior art. The pad would be extra-cochlea as it is placed onto the endosteum 142 that underlies the bone 140. The tubules and prongs exit the undersurface of the electrode pad and penetrate in a needle-like fashion through the endosteum 142 and into the internal cochlea such that the ends 74 of the prongs 72 are adjacent to dendrites and spiral ganglion cells 150 within and under the endosteum 148 and modiolus and osseous spiral lamina bone 146 of the cochlea.

FIG. 8 also illustrates the ganglion and dendrite growth achievable by the present invention. As shown in FIG. 8, ganglia growths 875, 877 are shown as extending into the interior of the cochlea, and growing to attach onto prongs 871, 873 and tubules 80, 82. As discussed above, the introduction of nerve growth promotion materials, such as neurotrophins, stems cells, etc., through the tubules 80 has the potential to cause the growth or re-growth of ganglia into the interior of the cochlea. Some of these growing ganglia 875, 877 may attach onto the prongs 871,873 and other ganglia 865, 866 may attach to tubules 80, 82 which would help to ensure that the signals reached and affected the ganglia to which the signals were targeted.

In the present on-lay technique a distinctly large strip of endosteum 142 overlying the bone 140 is uncovered. The area uncovered is distinctly different from the presently used "cochleostomy" technique for entering into the cochlea and inserting intra-cochlear implants. As such, it does not penetrate through the endosteum and it changes the area of bare endosteum in character with regard to the working surface size and texture. The entire endosteum of the basal turn of the cochlea overlying the scala tympani, the entire width and length of the basal turn, the entire middle turn, the entire intra-cranial basal and middle fossa turns, and the entire apical turn may be used. An area of cochlear endosteum large enough to give access to an on-lay electrode with or without needle penetration through the endosteum is created.

This new surgery technique may be termed an "extended soft surgery technique." The purpose of the present extended soft surgery technique is to bare a large area of endosteum 142 so that the electrode pad 62 of the extra-cochlear implant 60 can be positioned on the endosteum 142 by "on-laying" it.

The present "on-lay" technique is specifically designed so that one does not de-laminate endosteum to form a pocket. Rather, one drills away the covering cochlear bone 140 from over the endosteum 142 in the entire area in which the electrode pad 62 is to be placed. It is a technique similar to a "soft surgery" technique as described in the medical literature but not as circumscribed and small an area as in the medical literature since the entire area of exposure to the endosteum is "open", widely revealed, and directly accessible. There would not be pockets. There is direct access by instruments and electrodes to the endosteum. One reason one wants the endosteum widely revealed and open is because the number of electrode prongs and tubules that are placed need a large number of supply wires and hollow tubes connected to them. Therefore, a pocket would not be able to accommodate that volume of material. Also, the tubules and prongs are relatively narrow and long so that shoving them into a pocket would give rise to shear forces that would damage these structures.

The surgical technique for placing the on-lay electrode with or without prongs is that the cochlea promontory of the middle ear space would be visualized and thereafter, with a drill and suction-irrigation system, and a $CO_2$ laser, the bone overlying the scala tympani would be gently and deliberately drilled and dissected away to the point of the endosteum. The drilling would stop at the endosteum without penetrating or damaging the endosteum. In the present method, an actual long strip of bone would be removed, along the basal turn of the cochlea overlying the scala tympani.

Another surgical technique supporting the use of the different types of on-lay electrodes would be to create a second trough, running parallel to the scala tympani trough, along the scala vestibuli of the cochlea. Yet a third manifestation would be to remove the entire lateral wall of the basal turn and leave the endosteum intact over this entire area to accommodate an even larger electrode array, and allowing use of prongs/tubules in the three different (cross-sectional) cochlear spaces such as shown and described below with reference to FIG. 10.

After the endosteum has been bared, then the electrode would be placed onto the endosteum with the prongs touching the endosteum and then penetrating through at a specific angle so that they come to touch, lie close to or in the direction of the dendrites and spiral ganglion cells 150 for the scala tympani and the scala vestibuli; and within the cochlear duct for those types of prongs and tubules that are meant to be within the cochlear duct.

Since the prongs and tubules penetrate through the endosteum, perilymph and endolymph fluids could leak out of the cochlea through the mini-perforation points. As such, the electrode pad inner surface could have a sealant, such as for example, gelatinous hyaluronic acid, acting as a covering that would seal the openings in the endosteum. A fascia graft, such as is known in the art, may be placed over the entire pad 62 to internalize it and protect it against the invasion of bacteria, contact with air, and allow for the moist mucosal skin of the middle ear to grow over and cover the entire area and finally to scar into place in the long term.

It may be desired to secure the graft by packing the graft in place with an absorbable gelatin sponge until it heals completely. Also, fibrin glues are available that may be used. Ultimately, the wet muccous-membrane epithelium of the middle ear will heal over the fascia graft. The graft material will then scar to the edges of bone where one surgically drilled the extended soft surgery area as well as any exposed endosteum.

Additionally, access can be gained to the cochlea in the basal and middle turns of the middle cranial fossa approach. The middle cranial fossa approach is described in the literature with regard to access of the internal auditory canal and placement of intra-cochlear implants. When using the middle fossa approach for an on-lay implant, soft surgery would prepare an area of endosteum in the basal and/or middle turns similar to what was previously described for the lateral basal turn, followed by placement of an electrode pad, and would then be covered with a protective fascia graft.

With the on-lay extended soft surgery procedure described, everything is done straight on, without doing blind turns, or without employing the tunnel-pocket approach. One would be able to see and drill directly at the target as opposed to trying to perform blind tunnels or approach the area from difficult acute angles.

The apical turn approach is different from either of the basal or middle turn approaches just discussed. As the apical turn is very small, a small set of electrodes is placed. In this case, the tensor tympani muscle would be removed. This would allow drilling through the cochlear bone with eventual exposure of the apical cochlear turn's endosteum.

With the present open "extended soft surgery" technique, the large space of the middle ear is available for use and one is not space-constrained. One can place a larger "backbone" with the on-lay technique than one can if one were intra-cochlear or with use of a pocket. One is not constrained by space as with previous tunnel-pocket techniques.

Moreover, there may be and preferably is a sealant placed on the inner surface of the electrode pad. The sealant is preferably a gelatinous type of substance, such as for example, hyaluronic acid gel, that would help keep the perilymph from leaking out from the cochlea. A seal is formed at the apertures through which the prongs and tubules extend through the endosteum. A seal is also formed between the electrode pad and the endosteum when the pad is placed on the endosteum.

To fix the position of the electrode pad on the cochlea and to keep the prongs from falling out of the cochlea, a small electrode "tab" is attached to the pad that is used to attach the pad to the adjacent bone with an adhesive or other fixation method.

Figure 9:
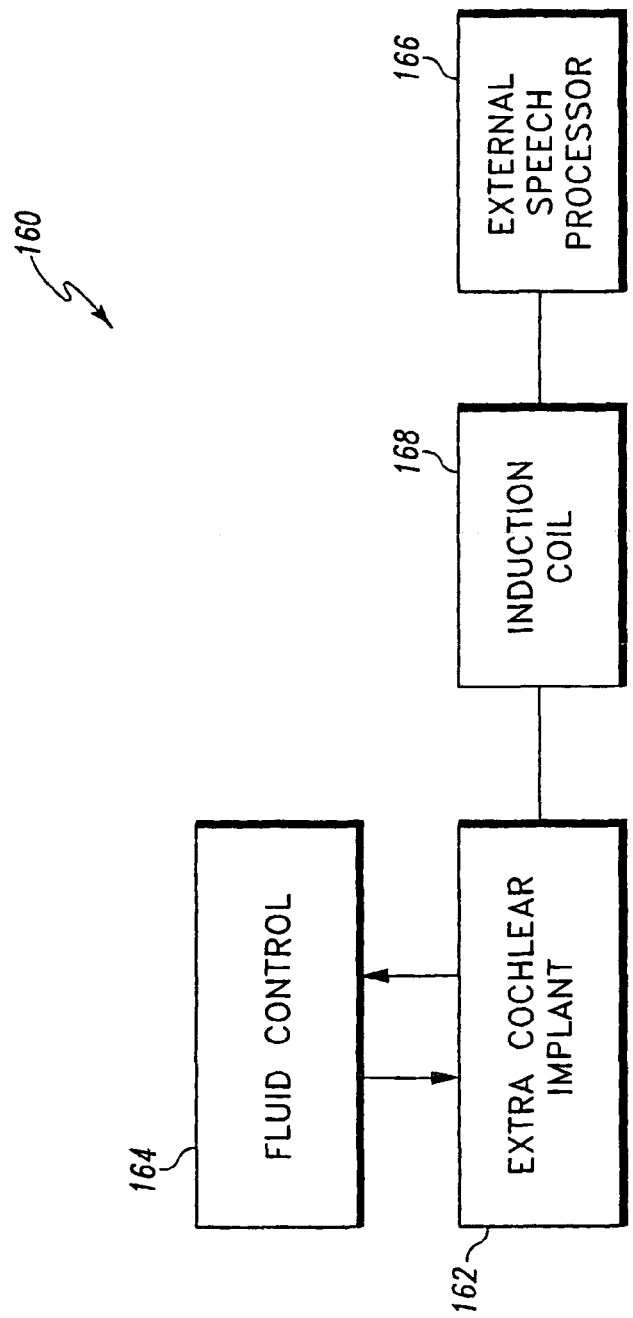
FIG. 9 is a block diagram illustrating operation of the present extra-cochlear implant.

Referring to FIG. 9, there is shown a block diagram of an extra-cochlear hearing aid system 160 that utilizes an extra-cochlear implant 162 that is fashioned in accordance with the present principles such as the exemplary embodiments described herein. The extra-cochlear implant 162 gathers its electrical energy stimulus trigger signal through a trans-cutaneous induction coil 168 disposed between the internal receiver stimulator of the extra-cochlear implant 162 and the external speech processor 166. The external processor, trans-cutaneous transmission, and internal receiver-stimulator device are generally going to be pretty similar to present and future intra-cochlear implants.

Different from presently known implants is that the hollow tubules and hollow prongs will need a supply tube and materials source. As such, the system 160 includes fluid control 164. The fluid control 164 may take several forms such as a subcutaneous reservoir, a subcutaneous pump, a mini osmotic pump such as or similar to the Alzet 2001 pump, a pump with a reservoir for refilling, and a trans-cutaneous tube for direct access to a pump or reservoir. Small catheter tubing would lead sequentially from the fluid source to the electrode backbone, pad and tubules. The supply source and tubing, in one form, has a self-sealing, detachable valve attachment to the electrode and/or implant device, and a bacterial filter.

Additionally, one additional feature of the present extra-cochlear implant, which may be necessitated by the introduction of fluid into the cochlea, is an exit or outlet valve as part of the fluid control 164 so that fluid can be removed from the cochlea in response to the fluid being placed into it. Theoretically, the fluid within the cochlea is non-compressible. There is some minimal "give" to the membranes and small amounts of fluid absorption. However, if one adds a volume of fluid to the cochlea and it has nowhere to go, it won't add. Therefore, one has to remove fluid as one injects fluid. An outlet valve would allow fluid to be removed. An outlet valve can either be placed at a distant site through another small soft surgery area or it could be at one end of the described electrode pads or it could be several valves along the electrode pad. The outlet valve would be a shorter hollow needle to allow the egress of fluid. The exiting fluid would fill a separate reservoir, shunt into the middle ear or mastoid, shunt into surrounding soft tissue such as the temporalis muscle, shunt outwards through a trans-cutaneous tube, or shunt into the extra-dural, intra-dural or intra cranial spaces. There may be use of a valve or valve system, an osmotic membrane, a bacterial micro-filter or combination thereof, and also a detachable self-sealing valve.

Figure 10:
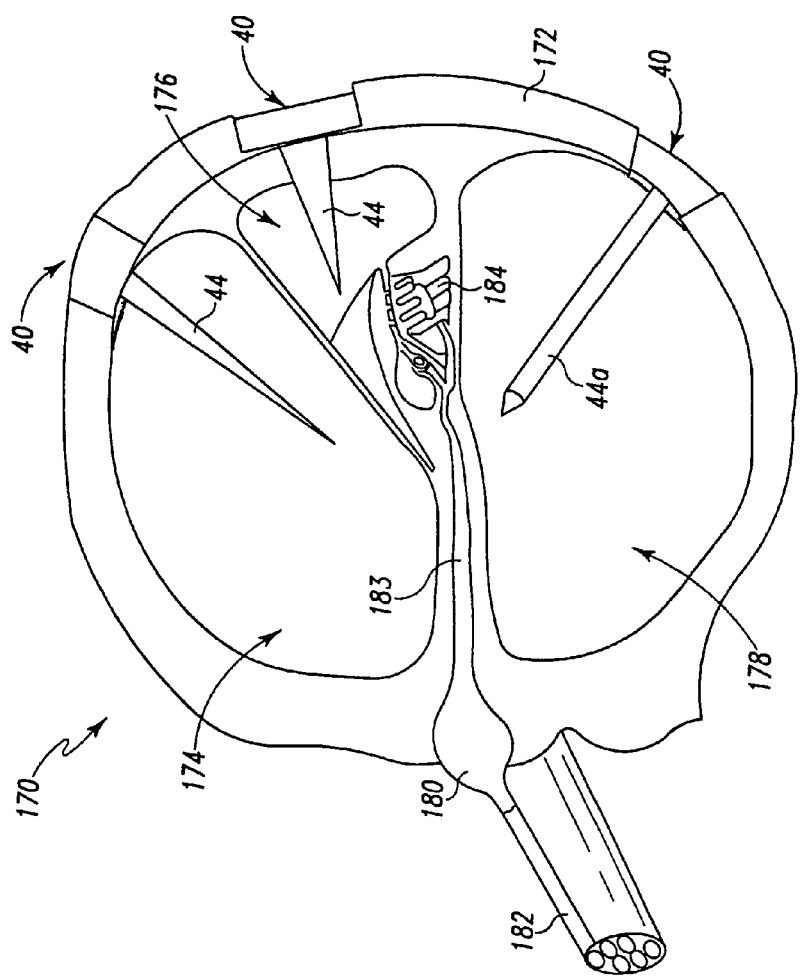
FIG. 10 is a cross-sectional view of the cochlea with electrodes in each cochlea chamber.

Rather than using a single extra-cochlear implant pad, it is useful in some situations to use multiple extra-cochlea implant pads. As such, attention is directed to FIG. 10. FIG. 10 depicts a cross-sectional view 170 of the cochlea, particularly showing the three ducts therein, i.e. the scala vestibuli 174, the scala tympani 178 and the cochlear duct 176. The ganglia cells 180 extend to the cochlear nerve 182. Dendrites 183 extend from the ganglia to the Cortis Organ 184. The position one places the primary extra-cochlear implant would be the lateral basal turn of the cochlea. Secondary sites could include the middle turn in the lateral portion of the cochlea, the basal and middle turns in the middle cranial fossa and the upper turn area on the lateral side of the cochlea.

FIG. 10 depicts three extra-cochlear implants, one implant for each cochlea chamber. Turning now to the three electrode pads 40, one would desire to place one at the basal turn and one at the middle turn so that one could wire and stimulate a greater number of tonotopic areas. As a generalization, the basal turn houses the highest frequencies; the middle turn, the middle frequencies; and the apical turn the lowest frequencies. Thus, by placing several electrode pads 40 over those areas more nerve tissue in more tonotopic areas would be stimulated.

It should be appreciated that the device shown in FIG. 10 employs electrode prongs/tubules in three different cross-sectional cochlear anatomic areas. There may be one, two or three area electrodes with prongs and tubules that are all in the cochlea at one cross-sectional point along the length of the cochlea. One may have one of these multi-electrode cross-sectional cochlea area arrays each on the basal, middle and directly on the apical turns simultaneously. So, this differs from the earlier discussion about the multi-electrode pads where one complete pad was on the basal turn, middle turn or on the apical turn. Alternately, the pad may cover several areas of different turns all at once as one "super-sized" pad.

The three different cross-sectional area electrode prongs or tubules are directed at three different areas. With regard to the cochlear duct, they may be used to encourage and stimulate nerve cells to grow into the osseous spiral lamina up into the previous area of the Organ of Corti. This may be one way to have regeneration of actual Organ of Corti elements as well as stimulating them. The scala vestibuli electrode approaches the cochlear nerve and spiral ganglion in one region. However, with growth of new nerve endings, due to chemicals such as neurotrophins, it may give rise to whole new areas of neural tissue and allow further neuro-stimulation. Some of these new areas would not normally be present as the nerves regenerate through and into the scala vestibuli fluid where they normally would not be found.

Normally, the nerve tissue is present from the cochlear nerve to the spiral ganglion area, up into the osseous spiral lamina, and then into the Organ of Corti within the cochlear duct. Since the cochlear duct contents have degenerated in deaf patients, the nerve cells will degenerate back to the spiral ganglion area and that's where one can now stimulate those with the electrodes through the fluids or through the bone.

Even within the scala tympani, the spiral ganglion is covered with a thin sheet of bone, so one is stimulating through the bone. This is a porous bone and through the porous elements, the nerve cells can give off growth of dendrites. With the scala tympani electrode components, the same thing can happen as when the spiral ganglion would send some of its fibers up into the scala vestibuli. In other words, the scala tympani plus the scala vestibuli are available for stimulation by the electrode. The more nerves that are stimulated the better the sound reproduction.

In another embodiment, the present on-lay electrode pad with the prongs and tubules could be used in combination with acoustical stimulation. In some cases, only the high frequencies have been lost in a hearing loss. Therefore, the upper frequency portions of the cochlea are still intact and hearing normally. The advantage of using an external electrode is that the actual internal cochlear fluid waves are not disrupted to the extent that would be experienced by placing an intra-cochlear electrode, and there would not be the anatomical disruption as with an intra-cochlear electrode. The electrode pad would be placed over the high frequency basal turn of the cochlea since the hearing structures are functioning at good capacity in the middle and apical cochlear turns.

The external on-lay electrode is less likely to disrupt fluids and micro-anatomy so it would be less traumatic by not being placed intra-cochlear in its entirety. Only the small needle-like penetrating prongs and tubules would extend into the cochlear fluid spaces with the pad and backbone of the electrode remaining extra-cochlear. The differentiation would be that if someone has good low frequency hearing (apical turn) and is deaf in the higher frequencies (basal turn), one may, for example, put an electrode array only on the basal turn of the cochlea, or just confine it to the basal and middle turn areas as an atraumatic on-lay electrode pad.

Electrical-acoustical hearing enhancement would use an ordinary hearing aid for low to mid frequencies and the on-lay implanted hearing aid device for mid to high frequencies. The overall hearing aid device with which the person would be implanted and use would be a combined partly acoustical, partly electrical stimulating device. Electrical Acoustical Stimulation has been described in the prior art for intra-cochlear implants.

While this invention has been described as having a preferred design, the present invention can be further modified within the spirit and scope of this disclosure. Variations, uses and adaptations of the invention using its general principles are thus intended to be covered. Moreover, departures from the present disclosure, as come within known or customary practice in the art to which this invention pertains and that fall within the limits of the appended claims, are also intended to be covered.

What is claimed:

1. An extra-cochlear hearing aid implant comprising:
a pad configured to overlie an endosteum of a cochlea; and
a plurality of electrodes extending from an underside of the pad and configured to pierce the endosteum of the cochlea and extend into an interior of the cochlea, the plurality of electrodes providing a plurality of different sound simulating electrical stimuli to at least one of a plurality of dendrites and plurality of spiral ganglia within the interior of the cochlea to foster hearing; and
wherein the pad is sized for placement on the endosteum of the cochlea and the pad, and plurality of electrodes, are sized and configured for subcutaneous implantation.

2. The extra-cochlear hearing aid implant of claim 1, wherein each of the plurality of electrodes is adapted to provide an electrical stimulus, and wherein the pad includes a plurality of electrical traces corresponding to the plurality of electrodes, the plurality of traces adapted to be connected to a source of electrical stimulus.

3. The extra-cochlear hearing aid implant of claim 2, further comprising a connector carried on the pad and electrically coupling the plurality of electrical traces with an electrically conductive wire.

4. The extra-cochlear hearing aid implant of claim 1, wherein the plurality of electrodes are variable in length.

5. The extra-cochlear hearing aid implant of claim 1, further comprising a fluid exchange system carried on the pad for supplying and withdrawing fluid to and from the an inside portion of the cochlea for improving at least one of the health and sound processing capabilities of the cochlea.

6. The extra-cochlear hearing aid implant of claim 1 wherein the plurality of electrodes have at least one of a generally cylindrical shape and a generally tapering shape.

7. The extra-cochlear hearing aid implant of claim 1, wherein the plurality of electrodes are needle-like, and are of sufficient strength to resist deformation upon piercing at least one of an endosteum and a modiolus bone.

8. The extra-cochlear implant of claim 1 wherein substantially all of the plurality of electrodes each includes an insulating covering extending over a portion of the electrode.

9. The extra-cochlear hearing aid implant of claim 8 wherein the electrodes include a base portion affixed to the pad, a tip portion placeable inside the cochlea, and a middle portion extending between the base portion and the tip portion, wherein the covering covers the base and the middle portions to facilitate the discharge of an electrical stimulus only at the tip portion.

10. The extra-cochlear implant of claim 9 wherein the covering comprises a coating applied to the base and middle portion of the electrode.

11. The extra-cochlear implant of claim 1 wherein the electrodes comprises an electrode selected from the group consisting of nanotubules, nanowires, and nanocable electrodes.

12. An extra-cochlear hearing aid implant comprising
a pad configured to subcutaneously overlie a portion of a cochlea;
a plurality of electrodes extending from an underside of the pad for providing a plurality of different sound simulating electrical stimuli to at least one of a plurality of dendrites and plurality of spiral ganglia and configured to pierce and extend into an interior of the cochlea, and a fluid exchange system carried on the pad for supplying withdrawing fluid to and from the interior of the cocklea for improving at least one of the health and sound processing capabilities of the cochlea.

13. The extra-cochlear hearing aid implant of claim 12, wherein the fluid exchange system comprises a hollow supply tube extending from the underside of the pad and configured to pierce and extend through an endosteum and into the cochlea, and a hollow withdrawal tube extending from the underside of the pad and configured to pierce and extend through the endosteum and into the cochlea.

14. The extra-cochlear hearing aid implant of claim 12, wherein the fluid exchange system comprises a plurality of hollow supply tubes extending from the underside of the pad and configured to pierce and extend into the cochlea, and a hollow withdrawal tube extending from the underside of the pad and configured to pierce and extend into the cochlea.

15. The extra-cochlear hearing aid implant of claim 12, wherein the pad includes a plurality of electrical traces corresponding to the plurality of electrodes, the plurality of traces adapted to be connected to a source of electrical stimulus.

16. The extra-cochlear hearing aid implant of claim 15, further comprising a connector carried on the pad and electrically coupling the plurality of electrical traces with an electrical wire.

17. The extra-cochlear hearing aid implant of claim 12, wherein the plurality of electrodes are variable in length.

18. The extra-cochlear hearing aid implant of claim 12, wherein the plurality of electrodes have a generally tapering shape.

19. The extra-cochlear heaving aid implant of claim 12 wherein the plurality of electrodes have a generally cylindrical shape, and are of sufficient strength to resist deformation upon piercing at least one of an endosteum and a modiolar bone.

20. The extra-cochlear hearing aid implant of claim 12 wherein the fluid exchange system supplies and withdraws neurotrophic material selected from the group consisting of neurotrophins, neuroptropins, antioxidants, vasoactive compounds, growth factors, antibiotics, antiglycemics, insulin, medications, nucleotides, amino acids, nutrients, cells, stem cells, and nanobots.

21. The system of claim 12, further comprising a fluid supply pump with a self-sealing detachable outlet valve and a bacterial filter.

22. The system of claim 12, wherein the fluid exchange system comprises a combined fluid and electrical system including at least two tubes, whereby the tubes conduct electrical stimuli into the cochlea in addition to acting as fluid conduits.

23. The extra-cochlear hearing aid of claim 12 wherein the supplied and withdrawn fluid comprises a neurotrophic fluid that comprises a slow release compound containing an active ingredient selected from the group consisting of neurotrophins, neurotropins, antioxidants, vasoactive compounds, growth factors, antibiotics, anti-glycemics, insulin, medications, nucleotides, amino acids, nutrients, cells, stem cells, nano-robots, and nanobots.

24. The extra-cochlear hearing aid of claim 23 wherein the slow release compound is attached to the electrodes.

25. The extra-cochlear hearing aid of claim 23, wherein the fluid exchange system includes at least one hollow supply tube extending from the underside of the pad and configured to pierce an endosteum of the cochlea and extend into the cochlea, and
wherein the slow release compound is attached to at least one of the electrodes and tube.

26. The extra-cochlear hearing aid of claim 25 wherein the slow release compound is disposed on at least one of the electrode and tube for preventing debris from blocking the tube.

27. The extra-cochlear hearing aid of claim 23, wherein the slow release compound is selected from the group consisting of pastes, coatings, bonded materials, fillings, shaped deposit and nano-containers.

* * * * *